United States Patent [19]

Sumiya

[11] Patent Number: 5,507,799
[45] Date of Patent: Apr. 16, 1996

[54] ABLATION APPARATUS FOR ABLATING AN OBJECT BY LASER BEAM

[75] Inventor: Toshifumi Sumiya, Aichi, Japan

[73] Assignee: Nidek Co., Ltd., Japan

[21] Appl. No.: 385,368

[22] Filed: Feb. 7, 1995

Related U.S. Application Data

[63] Continuation of Ser. No. 284,973, Aug. 4, 1994, abandoned, which is a continuation of Ser. No. 187,124, Jan. 27, 1994, abandoned, which is a continuation of Ser. No. 812,819, Dec. 24, 1991, abandoned.

[30] Foreign Application Priority Data

Dec. 28, 1990 [JP] Japan ..................... 2-416767

[51] Int. Cl.⁶ ........................... A61N 5/02
[52] U.S. Cl. .................. 606/5; 606/3; 606/13; 219/121.6; 219/121.74; 219/121.8
[58] Field of Search .......... 606/2–19; 128/897, 128/898; 219/121.6, 121.67, 121.7, 121.73, 121.74, 121.78, 121.8

[56] References Cited

U.S. PATENT DOCUMENTS

| | | | |
|---|---|---|---|
| 3,348,547 | 10/1967 | Kavanagh et al. | 606/4 |
| 4,069,823 | 1/1978 | Isakov et al. | 606/11 |
| 4,370,540 | 1/1983 | Davis et al. . | |
| 4,653,495 | 3/1987 | Nanaumi | 606/9 |
| 4,665,913 | 5/1987 | L'Esperance | 606/5 |
| 4,732,148 | 3/1988 | L'Esperance et al. . | |
| 4,911,711 | 3/1990 | Telfair et al. | 606/5 |
| 4,941,093 | 7/1990 | Marshall et al. . | |
| 4,994,058 | 2/1991 | Raven et al. . | |
| 5,102,409 | 4/1992 | Balgorod . | |
| 5,108,388 | 4/1992 | Trokel . | |
| 5,163,934 | 11/1992 | Munnerlyn . | |

FOREIGN PATENT DOCUMENTS

| | | |
|---|---|---|
| 63-150069 | 6/1988 | Japan . |
| 63-289519 | 11/1988 | Japan . |
| 63-289519A | 11/1988 | Japan . |

Primary Examiner—David M. Shay
Attorney, Agent, or Firm—Finnegan, Henderson, Farabow, Garrett & Dunner

[57] ABSTRACT

An ablation apparatus for ablating an object to a uniform depth by a laser beam. The laser may be an excimer laser, having non-uniform beam intensity of Gaussian distribution and like. Therefore the laser beam is scanned to the non-uniform intensity distribution and irradiated on the surface of the objection, whereby uniform depth of ablation is achieved. The apparatus is preferably applied to the operation of the cornea.

14 Claims, 6 Drawing Sheets

FIG. 2
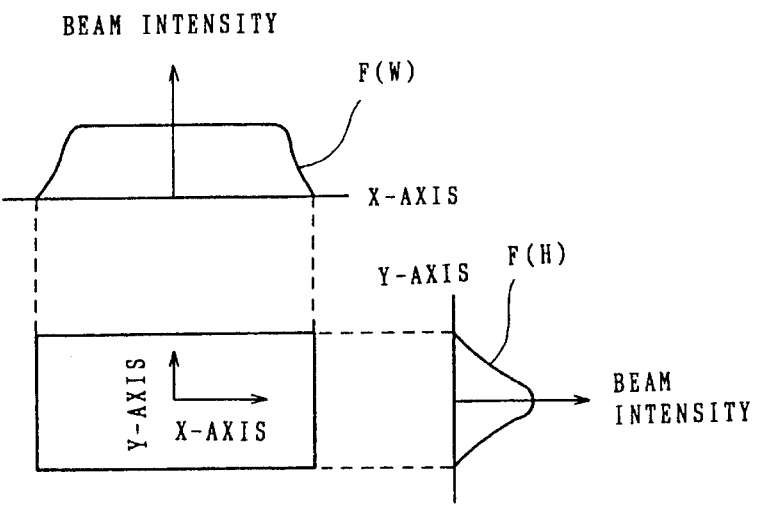
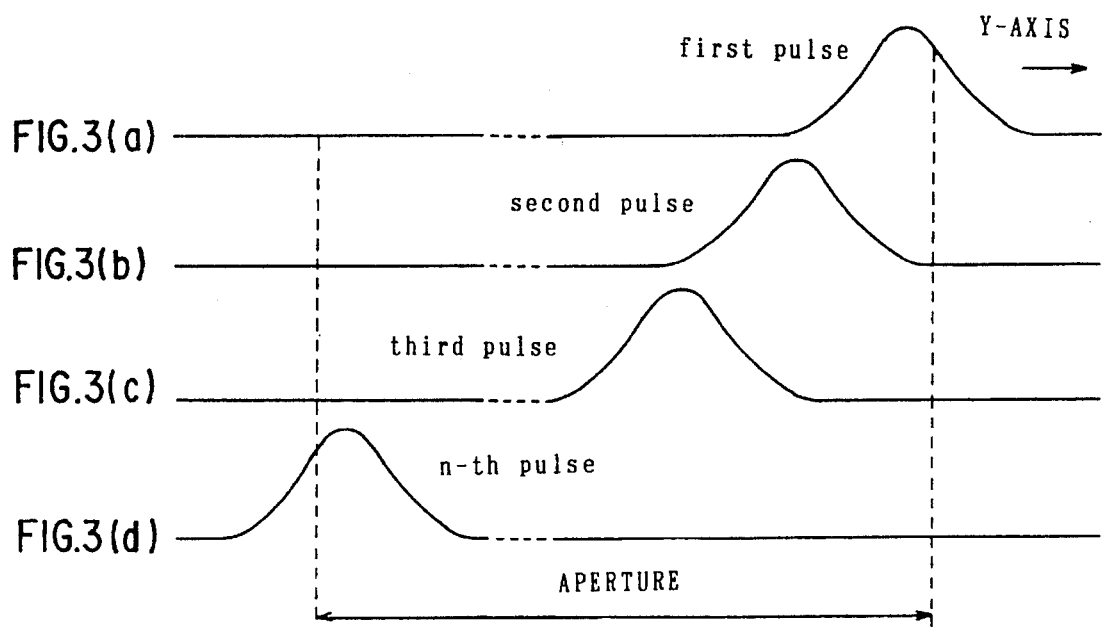
FIG.3(a)
FIG.3(b)
FIG.3(c)
FIG.3(d)

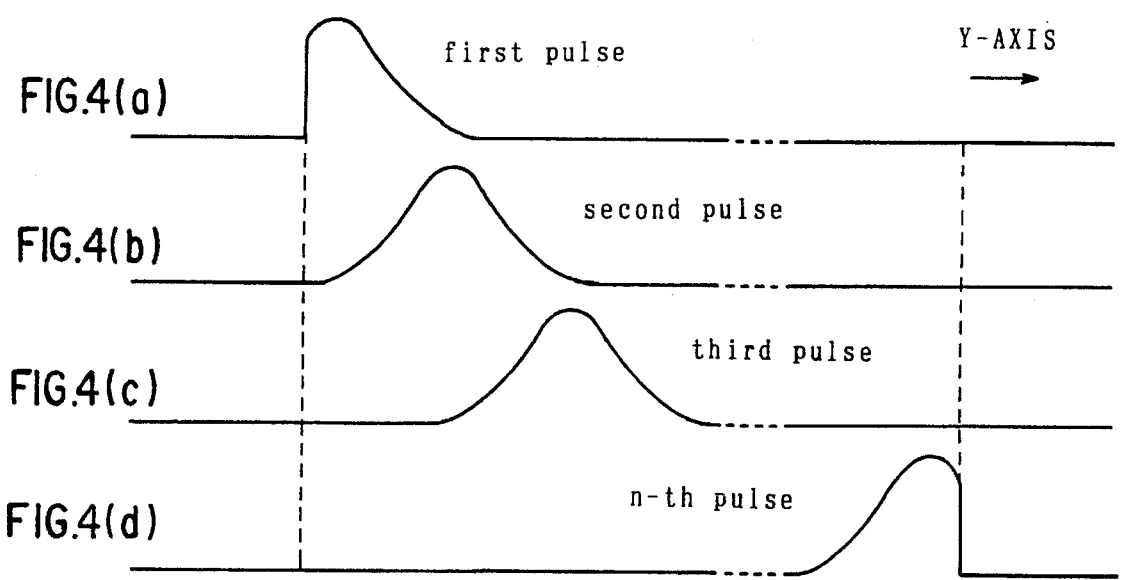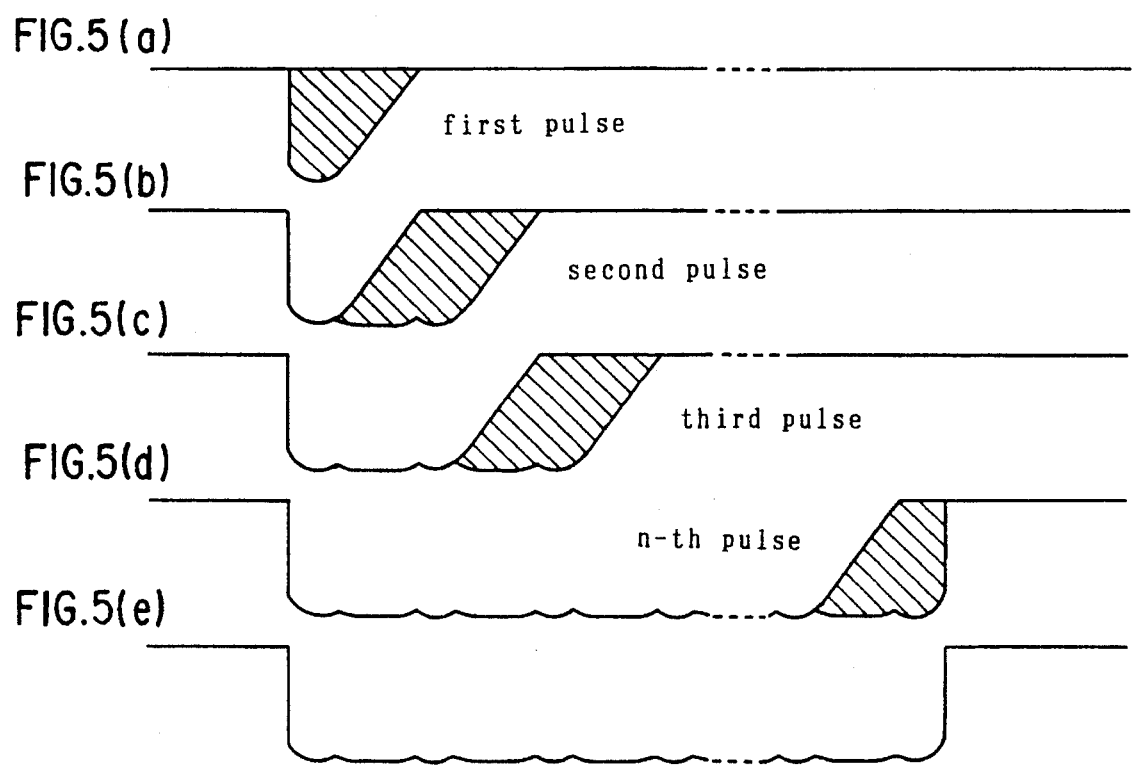

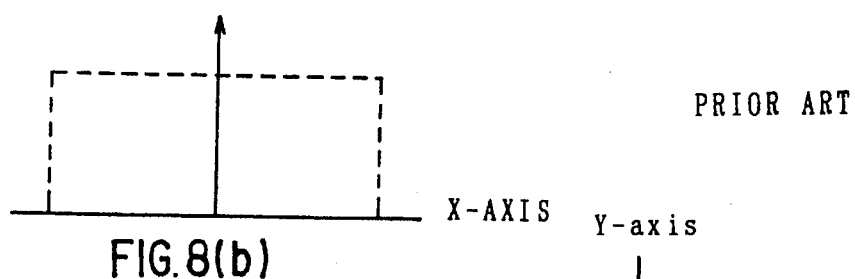
FIG.8(b)
PRIOR ART
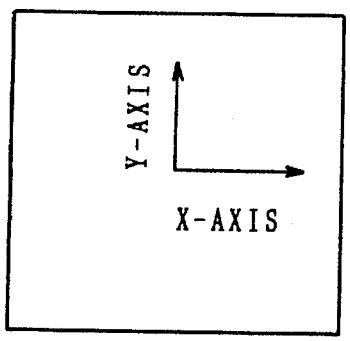
FIG.8(a)
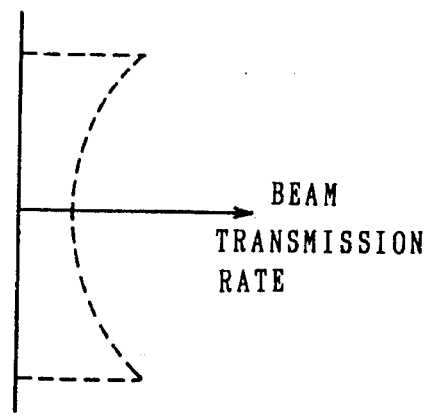
FIG.8(c)
FIG. 9
PRIOR ART
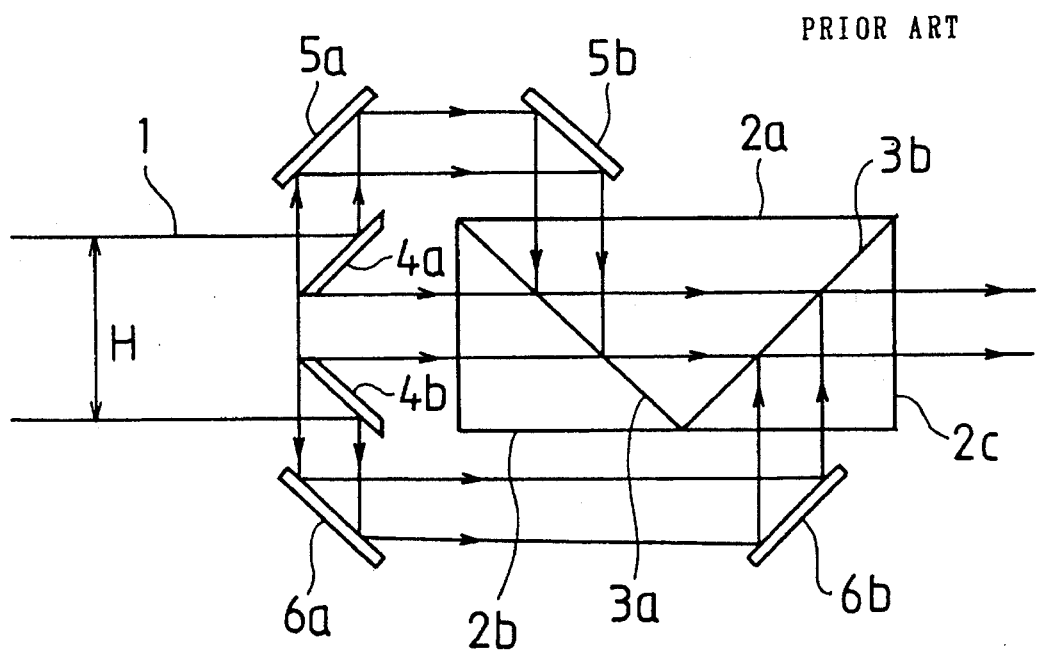

ABLATION APPARATUS FOR ABLATING AN OBJECT BY LASER BEAM

This application is a continuation of application Ser. No. 08/284,973 filed Aug. 4, 1994, now abandoned, which is a continuation of application Ser. No. 08/187,124 filed Jan. 27, 1994, now abandoned, which is a continuation of application Ser. No. 07/812,819 filed Dec. 24, 1991, now abandoned.

BACKGROUND OF THE INVENTION

1. Field of the Invention

The present invention relates to an ablation apparatus for ablating an object by laser beam (typically an excimer laser) having a non-uniform beam intensity of Gaussian distribution in one direction and a uniform beam intensity in the vertical direction. More particularly, the present invention relates to an ablation apparatus for controlling ablation of a surface of a cornea by a laser beam to correct the curvature of the cornea.

2. Description of the Related Art

Recently, some methods have been proposed for correcting the refraction of an eye by ablating the surface of the cornea to change the curvature of the cornea. In these methods, it is necessary to control the depth of the ablation area so that it is uniform. This has been accomplished by controlling the intensity distribution of the laser beam being used for ablation such that it is constant.

For example, Japanese Laid-open Patent Application No. 63-150069 (U.S. Pat. No. 4,911,711) proposes homogenizing a laser beam by using a filter having a special beam transmission distribution, and also by reflecting the laser beam.

In the filter method, the laser beam passes through a filter having a beam transmission distribution opposite to the beam intensity distribution of the laser beam, whereby the beam intensity is reduced at the part of high beam intensity area of the laser beam and a homogenized beam intensity distribution is attained.

If the laser beam from, for example, an excimer laser, has a beam section as shown in FIG. 7(a), the beam intensity distribution in the X-axis direction is uniform as shown in FIG. 7(b), and the Gaussian beam intensity distribution and like in the Y-axis direction has a maximum curvature in the central part of the laser beam as shown in FIG. 7(c). The laser beam will pass through the filter with a beam transmission distribution in the Y-axis which is low at the central part of the filter area as shown in FIG. 8(c) (in this case, the beam transmission distribution in the X-axis direction is uniform as shown in FIG. 8(b)). The intensity of the high intensity part (the central part of the intensity distribution shown in FIG. 7(c) is reduced at the low transmission part of the filter (central part of the transmission distribution shown in FIG. 8(c)).

At the low laser beam intensity part (both end parts of the intensity shown in FIG. 7(c), the laser beam passes through highly transmissive parts of the filter (both ends part of the transmission distribution shown in FIG. 8(c)), and the beam intensity is only slightly reduced. Consequently, the intensity of the transmitted laser beam becomes the same at the low part (both end portions) and the high part (central portion), and uniformity of the beam intensity is attained.

The method to homogenize a laser beam by reflecting it distributes the laser beam to a plurality of parts and synthesizes them so that the beam intensity is homogenized. Such a homogenizing apparatus is shown in FIG. 9. The apparatus comprises a central triangular optical prism 2a, two smaller outer triangular prisms 2b, 2c, first and second beam splitting interfaces 3a, 3b, an inlet assembly of spaced reflectors 4a, 4b to divide the laser beam, and outer pairs of reflectors 5a, 5b and 6a, 6b.

The reflectors 4a, 4b each reflect an outer one-third portion of the beam with an expanded height dimension H, to the direction of the reflectors 5a, 6a for further reflection by reflectors 5a, 6a to offset the outer portions from the path of the central one-third portion. At the location of the operative part of the beam splitter 3a, the reflector 5b deflects the divided upper one-third fraction into additive relation with the central one-third fraction. At the location of the operative part of the beam splitter 3b, the reflector 6b reflects the divided lower one-third fraction into an additive relation with the central one-third, and with the already added upper one-third fraction.

FIG. 10 depicts the functional result of what has been described in connection with FIG. 9. The Gaussian intensity profile P of a beam shown by dashed lines includes an upper portion that is picked off and transmitted by reflectors 4a, 5a, 5b for addition at beam splitting interface 3a with the central portion. The displaced upper portion is indicated by the alternate long and short dash line P'.

Similarly, the lower portion of the profile P" indicated by alternate long and short dash line is picked off and transmitted by reflectors 4b, 6a, 6b for addition at beam splitting interface 3b with the already combined upper and central portions. The net result is a beam output which has the H/3 dimension of the central one-third portion and which has an added intensity distribution substantially as indicated by the solid-line profile $P_R$.

Another proposed method is shown in Japanese Laid-open Patent Application No. 63-289519 which uses a cylindrical lens array including a dense array of small, cylindrical lenses arranged parallel to the X-direction. FIG. 11 depicts an arrangement where the laser beam arrives at an irradiation surface S, by passing through a toric lens 7 and the cylindrical lens array 8.

After the laser beam is converged by the toric lens 7 having a strong beam converging nature in the Y-direction and a weak beam converging nature in the X-direction, the beam passes to the cylindrical lens array 8. The refraction of the laser beam in the Y-direction by the cylindrical lens array is randomized, and the intensity distribution is averaged equally on the irradiation surface S.

There are several problems with the methods mentioned above. In the method which uses the beam transmission filter having a special beam transmission distribution, it is difficult to produce the filter having the proper curvature and a unified intensity distribution may not be obtained because the beam transmission distribution is inaccurate. Also, if the intensity distribution of the laser beam is changed, or the beam axis is misaligned, the intensity distribution of the laser beam could not be counterbalanced by the beam transmission distribution of the filter. Also, there is a problem in that the degree of beam transmission of the high beam intensity area must be reduced to conform with the low beam intensity area, and the loss of energy is unacceptable.

In the homogenizing method using laser beam reflection by a plurality of mirrors, the structure becomes complex and it takes much time to adjust an arrangement of components. If the intensity of the laser beam is changed or the beam axis is misaligned, a uniform intensity distribution cannot be obtained and the energy loss is unacceptable when the laser beam is recombined after being divided by the beam splitter.

In the method using the cylindrical lens array, the production of the cylindrical lens array is complex and requires much time to produce.

SUMMARY OF THE INVENTION

Accordingly, it is an object of the present invention to overcome the above problems and to provide an ablation apparatus for ablating an object by laser beam to a uniform depth.

Another object of the present invention is an ablation apparatus that uses optical energy efficiently to accomplish uniform depth of ablation.

It is a further object to provide an ablation apparatus that has a simple structure and does not use a complex optical system or optical elements that are difficult to produce.

The above and further objects and novel features of the invention will be attained by an ablation apparatus for ablating the surface of an object by a laser beam having an intensity distribution of Gaussian distribution to one direction and a uniform beam intensity in another direction comprising a laser source for emitting a laser beam, scanning means for scanning the laser beam in a direction of non-uniform intensity distribution of the laser beam, and irradiation means for irradiating the laser beam scanned by the scanning means on an object to be ablated.

BRIEF DESCRIPTION OF THE DRAWINGS

The invention will be described in detail with reference to the following drawings, wherein:

FIG. 2 is a schematic diagram of a horizontal (X-axis) beam intensity profile and a vertical (Y-axis) beam intensity of a laser beam from an excimer laser as used in the embodiment of FIG. 1;

FIGS. 3(a) through 3(d) are diagrams showing the laser beam intensity profile in the vertical (Y-axis) direction on an aperture;

FIGS. 4(a) through 4(d) are diagrams showing the laser beam intensity profile in the vertical (Y-axis) direction on the cornea of an eye;

FIGS. 5(a) through 5(e) are diagrams to explain the condition (process) of ablation of FIG. 4;

FIGS. 8(a) through 8(c) are diagrams to explain the first example of a prior art device;

FIG. 9 is a diagram to explain a second example of a prior art device;

DETAILED DESCRIPTION OF A PREFERRED EMBODIMENT

A detailed description of a preferred embodiment of an ablation apparatus embodying the present invention will now be given referring to the accompanying drawings.

Figure 1:
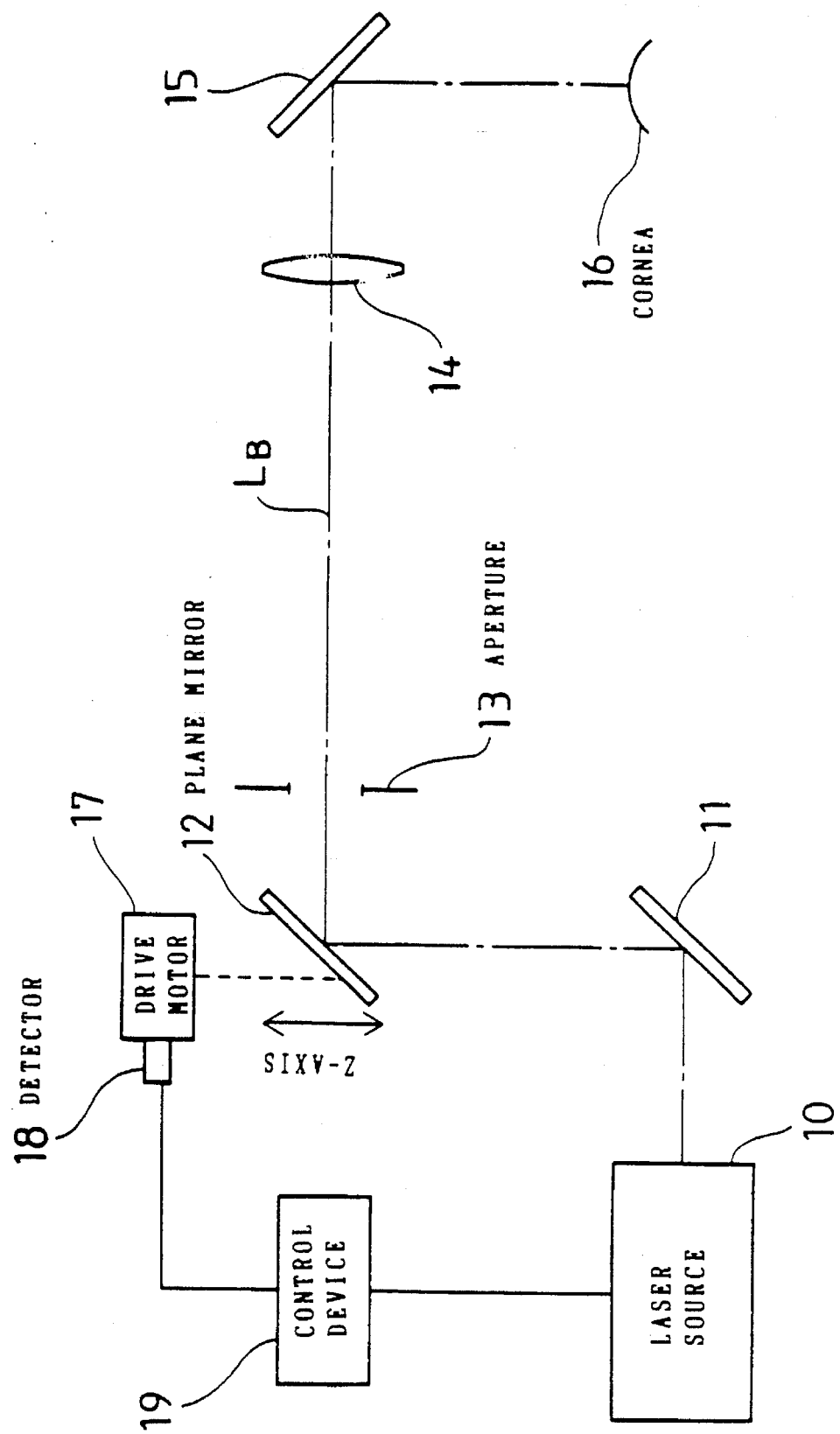
FIG. 1 is a schematic diagram of the arrangement of components of the invention.

As shown in FIG. 1, an optical system of the ablation apparatus includes a laser source 10 (preferably an excimer laser), plane mirrors 11, 12, 15 for deflecting the laser beam $L_B$ emerging from the laser source 10, an aperture 13 with a variable diameter located in the optical path between the mirrors 12, 15, and a projection lens 14 for projecting the laser beam $L_B$ passing through the aperture 13 to a cornea 16 via mirror 15.

The laser beam $L_B$ emerging from the laser source 10 is deflected 90° by the plane mirror 11 and another 90° by the mirror 12 while it remains in the same plane. After the laser beam passes through the aperture 13, the laser beam $L_B$ is also deflected 90° by the plane mirror 15 in the same plane, and projected to the surface of the cornea 16.

Although the laser beam is diffused when passing through the aperture 13, it becomes condensed by the projection lens 14. The projection lens 14 is conjugated with the aperture 13 and the cornea 16, and the laser beam passing through the aperture 13 in a confined space is projected on the surface of the cornea 16 such that an ablation area of the cornea is restricted.

The cornea is provided at a position having a predetermined positioning relation for the apparatus.

The beam section profile of the laser beam emitted from the laser source 10 of FIG. 1, has an almost uniform intensity distribution F(W) in the horizontal direction (X-axis direction) of the laser beam, but the beam intensity distribution in the vertical direction (Y-axis direction) is a Gaussian distribution F(H).

The plane mirror 12 of FIG. 1, is movable parallel to the Z-axis by a driving motor 17, and the position of the mirror 12 (amount of movement) is detected by a positioning detector 18. The positioning detector 18 may comprise, for example, a rotary encoder attached to a driving axis of the mirror's driving motor 17.

The positioning detector 18 and the laser source 10 are connected to a control device 19, and the laser pulses are emitted based on an output signal of the positioning detector 18. The operation of the present apparatus is controlled by a microcomputer of the control device 19.

As described above, the mirror 12 moves parallel to the Z-axis direction of FIG. 1, whereby the laser beam is moved in parallel in the direction of the Gaussian distribution. The plane mirror 12 moves synchronously to the laser pulse outputted by laser, source 10, and after one or more laser pulses have been outputted at a certified position of the plane mirror 12, the mirror 12 moves to a next position, and again at that position of the mirror 12 one or more laser pulses will be further outputted as the mirror 12 moves further to a next position. This moving operation is repeated from the one end of the aperture 13 to the other end. This means that the irradiation of the laser beam is repeated on the ablation area of the cornea 16 at a determined interval (by one or more of the laser pulses) so that the pulses are combined and a uniform depth of ablation is achieved.

The moving amount of the plane mirror 12 is determined by correlation among several components, e.g., the depth of ablation, the degree of uniformity required or the intensity and intensity distribution of the laser beam and the like. The adjustment of the laser beam's intensity or the ablation's depth per one pulse may be obtained by adjusting the output power of the laser source within a certain range.

For convenience of explanation, it may be assumed that the plane mirror 12 moves for every pulse although such a one-to-one relationship is not required for the present invention. FIGS. 3(a) through 3(d) show the change of the intensity distribution of the laser beam in Y-axis direction on the aperture 13. FIGS. 4(a) through 4(d) show the change of the intensity distribution in the Y-axis direction on the cornea 16. FIGS. 5(a) through 5(e) show the condition (process) of the ablation on the cornea.

When a first pulse of the laser beam having the intensity distribution shown in FIG. 3(a) on the aperture 13 is irradiated on the cornea 16 by the projection lens 14, the intensity distribution on the cornea 16 is as shown in FIG. 4(a). At that time, the cornea 16 is ablated by the irradiation of the laser beam, as shown with oblique lines in FIG. 5(a). When a second pulse of the laser beam is irradiated, as the plane mirror 12 has been moved in the Z-axis direction, the intensity distribution on the aperture 13 is changed as shown in FIG. 3(b). Accordingly, the intensity distribution projected on the cornea 16 by the projection lens 14 is as shown in FIG. 4(b), and the cornea 16 is further ablated as shown with oblique lines in FIG. 5(b). The third pulse of the laser beam produces an intensity distribution on the aperture 13 as shown in FIG. 3(c) and the intensity distribution on the cornea 16 as shown in FIG. 4(c), whereby the area of the cornea shown with oblique lines in FIG. 5(c) is further ablated. Similarly, fourth and subsequent laser pulse up to the n-th pulse of the laser beam, cause intensity distribution on the aperture 13 as shown in FIG. 3(d). FIGS. 4(d) shows the intensity distributions on the cornea 16 and the area shown in FIG. 5(d) with oblique lines is ablated.

By moving the plane mirror 12 parallel to the Z-axis direction synchronously with respect to the laser pulse and irradiating the laser beam while scanning it in the direction of its non-uniform intensity distribution the cornea 16 is ablated with an almost uniform depth.

Figure 6A:
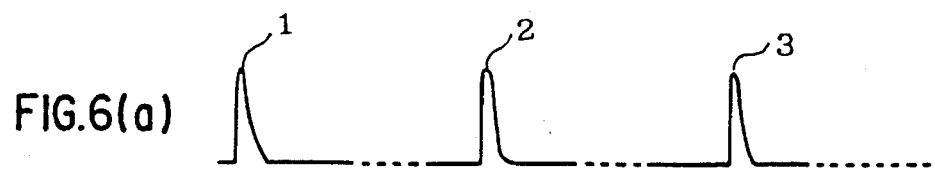
FIGS. 6(a) and 6(b) are timing charts to explain the movement control of the plane mirror 12 shown in FIG. 1 with respect to the laser pulse.
Figure 6B:
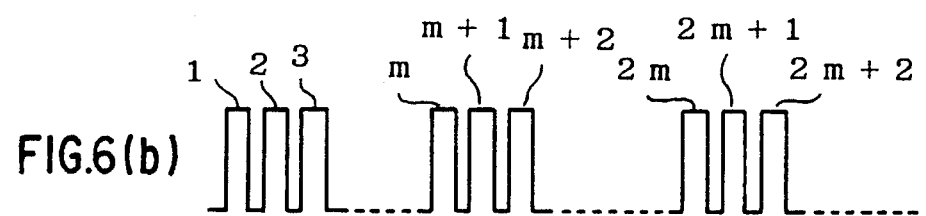
Figure 7B:
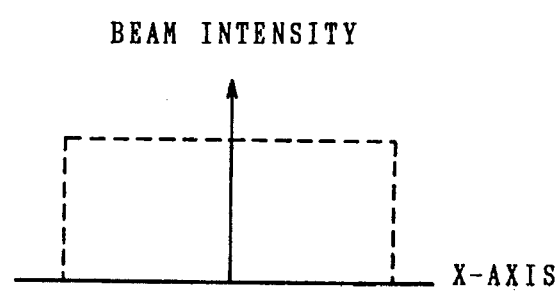
FIGS. 7(a) through 7(c) are diagrams to explain a general example of the energy distribution of a laser beam, e.g., an excimer laser beam.
Figure 7A:
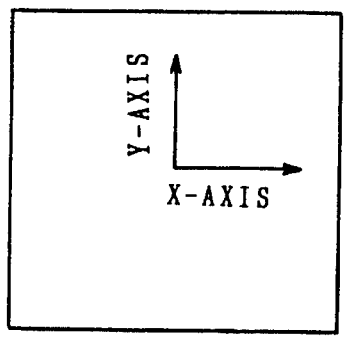
Figure 7C:
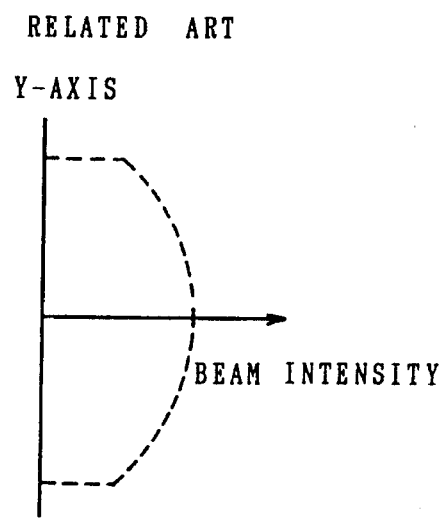
Figure 10:
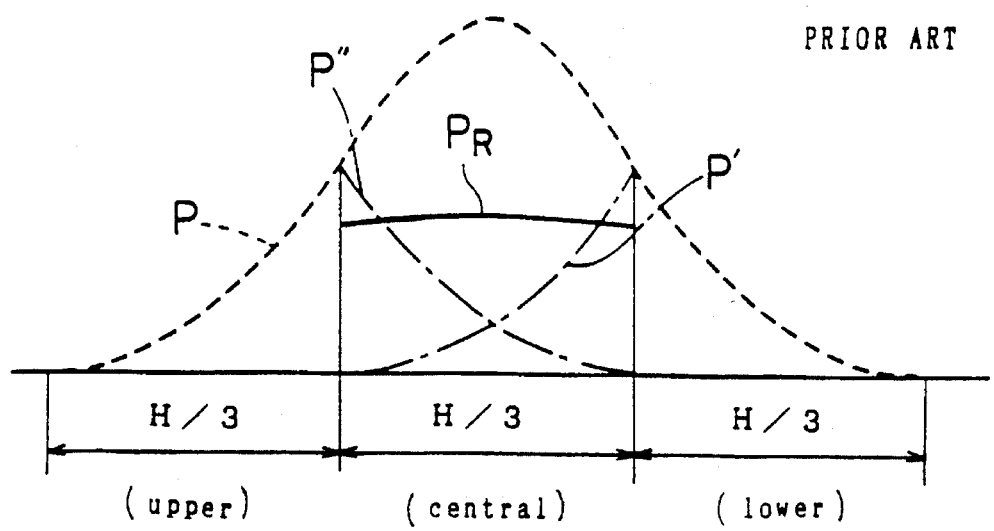
FIG. 10 is a diagram to explain the beam intensity distribution obtained by the device shown in FIG. 9.
Figure 11:
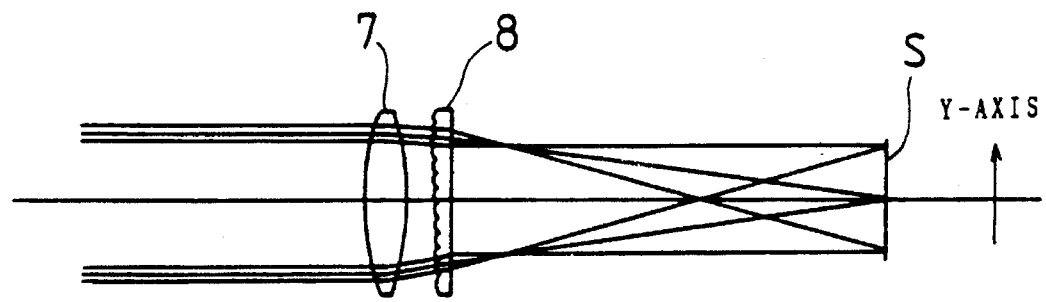
FIG. 11 is a diagram to explain a third example of a prior art device.

FIGS. 6(a) and 6(b) are timing charts to explain the timing of a control mechanism that moves the plane mirror 12 synchronously with respect to the laser pulses. In the FIG. 6(a), the output pulse of the laser beam is shown and FIG. 6(b) shows output signals of the detector 18 detecting the position of the plane mirror 12.

The amount of movement of the plane mirror 12 to obtain a uniform ablation depth employs an m-pulse output signal of the position detector 18.

If the output signal of the position detector 18 detecting the position of the plane mirror 12 at the time of the first laser beam pulse is the first detecting pulse, the plane mirror 12 is moved so that the m+1-th output signal is outputted at the time of the second laser pulse and 2m+1-th output signal is outputted at the time of the third laser pulse so that the laser pulse is emitted each m-th pulse of the output signal of the position detector 18. By repeating such laser beam pulses, uniform ablation by the laser beam irradiation is accomplished. It is proper that the laser is used in a condition of about 20 to 50 Hz, so that operation time is shortened and the load of the laser should be decreased.

The words that shows direction in the above description of the embodiment, are used only to describe a relation of the direction of the laser beam's energy distribution, and other directions may be employed.

The present invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. An ablation apparatus for ablating a surface of an object, comprising:

laser source means for emitting a laser beam having a non-uniform intensity of a Gaussian distribution in one direction and a uniform beam intensity in another direction;

scanning means for scanning the laser beam only in the direction of the non-uniform intensity of the laser beam; and irradiation means for irradiating the laser beam scanned by the scanning means on an object to be ablated.

2. The apparatus according to claim 1, wherein the laser source comprises an excimer laser.

3. The apparatus according to claim 1, wherein the laser source means comprises a laser capable of emitting a laser beam having an intensity suitable for ablating a surface of a cornea of an eye.

4. The apparatus according to claim 1, wherein the irradiation means comprises an aperture diaphragm to restrict an area to be irradiated on an object, the aperture diaphragm having an opening smaller than the laser beam and in the direction of the uniform beam intensity.

5. The apparatus according to claim 1, wherein the laser source comprises means for emitting an ultra-violet laser beam.

6. The apparatus according to claim 1, wherein the irradiation means comprises variable aperture means for controlling an aperture through which the laser beam is passed and projection lens for irradiating the laser beam passing through the aperture onto the object.

7. The apparatus according to claim 8, wherein the projection lens is conjugate with said aperture and the surface of the object to be ablated to project an image of the aperture on the surface of an object to define the area to be ablated.

8. The apparatus according to claim 1, wherein the scanning means comprises a reflection type optical element for reflecting the laser beam and moving means for moving the reflection-type optical element in the direction of the non-uniform intensity distribution of the laser beam.

9. The apparatus according to claim 8, wherein the reflection-type optical element comprises a reflection mirror.

10. The apparatus according to claim 8, wherein the moving means comprises a driving motor.

11. The apparatus according to claim 8, further comprising position detecting means for detecting a position of the reflection-type optical element.

12. The apparatus according to claim 11, wherein the position detecting means comprises a rotary encoder.

13. The apparatus according to claim 12, further comprising control means for controlling emission of the laser beam by the laser source.

14. A method for ablating an object comprising the steps of:

irradiating a laser beam having a non-uniform intensity distribution of a Gaussian distribution in one direction and a uniform beam intensity in another direction;

scanning the laser beam only in the direction of the non-uniform intensity distribution of the laser beam; and ablating the object using the scanned laser beam.

* * * * *